United States Patent
Xu

(10) Patent No.: US 10,005,726 B2
(45) Date of Patent: Jun. 26, 2018

(54) RIBOCICLIB INTERMEDIATE AND PREPARATION METHOD THEREFOR

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days. days.

(21) Appl. No.: 15/821,754

(22) Filed: Nov. 22, 2017

(65) Prior Publication Data

US 2018/0093950 A1 Apr. 5, 2018

Related U.S. Application Data

(63) Continuation of application No. PCT/CN2016/081939, filed on May 13, 2016.

(30) Foreign Application Priority Data

Jun. 4, 2015 (CN) .......................... 2015 1 0300181

(51) Int. Cl.
  *C07D 207/36* (2006.01)
  *C07D 471/04* (2006.01)
(52) U.S. Cl.
  CPC ......... *C07D 207/36* (2013.01); *C07D 471/04* (2013.01)

(58) Field of Classification Search
  CPC .................................................. C07D 207/36
  See application file for complete search history.

(56) References Cited

U.S. PATENT DOCUMENTS

2012/0115878 A1 5/2012 Calienni et al.

FOREIGN PATENT DOCUMENTS

| CN | 103788100 A | 5/2014 |
| CN | 105037236 A | 11/2015 |
| WO | 2010020675 A1 | 2/2010 |

*Primary Examiner* — Shawquia Jackson
(74) *Attorney, Agent, or Firm* — Perkins Coie LLP

(57) ABSTRACT

Disclosed are an intermediate N-cyclopentyl-2-methoxy-5-(N,N-dimethyl-formamido)-3-pyrrylformonitrile (II) for preparing ribociclib and a preparation method therefor. The preparation method comprises the following preparation steps: carrying out halogenating reaction on N,N-dimethyl-2-carbonyl-propanamide (IV) to obtain N,N-dimethyl-1-halo-2-carbonyl-propanamide (V); carrying out substitution reaction on the intermediate (V) and malononitrile to prepare N,N-dimethyl-1,1-dicyano-3-carbonyl-butyramide (VI); carrying out cyclization reaction on the intermediate (VI) to prepare 2-methoxy-5-(N,N-dimethyl-formamido)-3-pyrrylformonitrile (VII); and carrying out coupling reaction on the intermediate (VII) and bromocyclopentane to obtain the intermediate N-cyclopentyl-2-methoxy-5-(N,N-dimethyl-formanido)-3-pyrrylformonitrile (II) for preparing ribociclib. The intermediate (II) and N-[5-(1-piperazino)-2-piperidyl]guanidine (III) are subjected to condensation reaction to prepare ribociclib. The preparation method has the advantages of accessible raw materials, simple process, high economy and environmental friendliness, and is suitable for industrial production.

11 Claims, No Drawings

RIBOCICLIB INTERMEDIATE AND PREPARATION METHOD THEREFOR

CROSS REFERENCE TO RELATED APPLICATIONS

This application is a continuation of PCT/CN2016/081939 filed May 13, 2016, which claims priority to CN201510300181.4 filed Jun. 4, 2015, both of which are incorporated herein by reference.

TECHNICAL FIELD

The invention belongs to the technical field of organic synthetic route design and preparation of a crude drug and an intermediate therefor, and particularly relates to a preparation method of ribociclib as a medicine which is possibly used for treating a breast cancer.

BACKGROUND ART

Ribociclib is a high-specificity cell cycle-dependent kinase (CDK4/6) inhibitor which is developed by the Novartis Company and is orally effective, and the code of ribociclib is LEE011. LEE011 is a dual inhibitor of CDK4/6, and can remarkably inhibit growth of 12 of 17 kinds of neurocytomas. The drug is in stage-III clinical test currently, and is used for treating an advanced breast cancer. Owing to successful research of the drug, another important choice will be provided for patients suffering from the metastatic breast cancer. Because the drug does not have a standard Chinese name, the applicant transliterates ribociclib into 'Ruiboxi'ni' herein.

The chemical name of ribociclib (I) is 7-cyclopentyl-N,N-dimethyl-2-{[5-(piperazine-1-yl)piperidine-2-yl]amino}-7H-pyrrole[2,3-d]pyrimindine-6-formamide, and the structural formula of ribociclib is as follows:

(I)

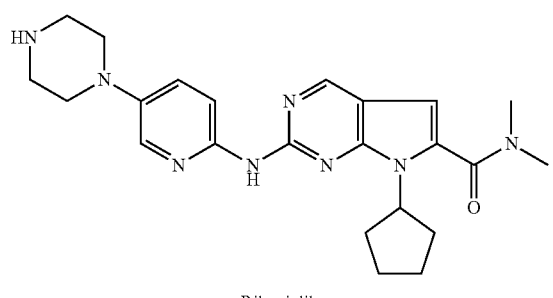

Ribociclib

Literatures such as PCT patent WO2010020675 of the original research company and United States patent US20120115878 have reported a synthetic method of ribociclib, and preparation steps of the synthetic method comprise synthesis of intermediates A and B and a process of preparing ribociclib by condensation of the A and the B.

Synthesis of intermediate A

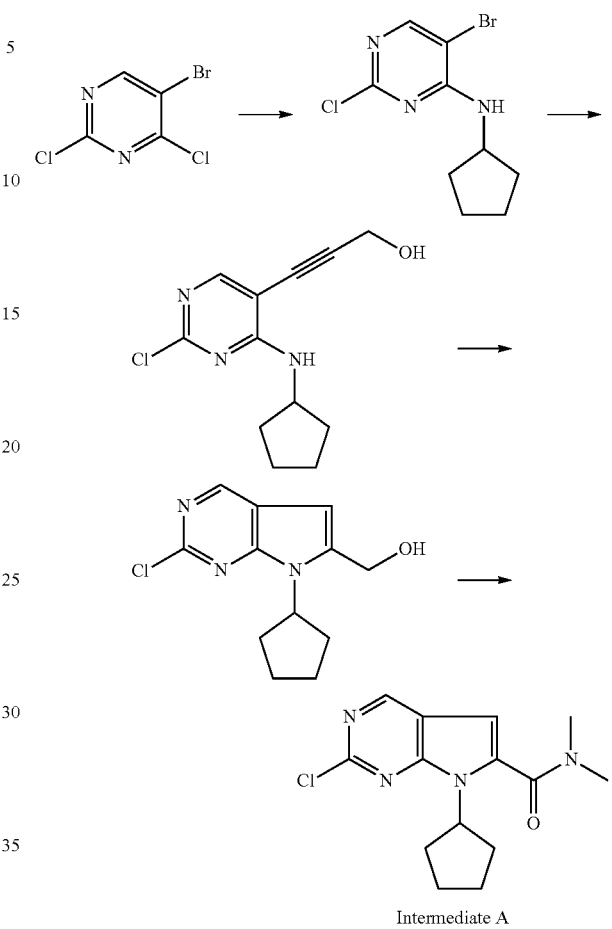

Intermediate A

Synthesis of intermediate B

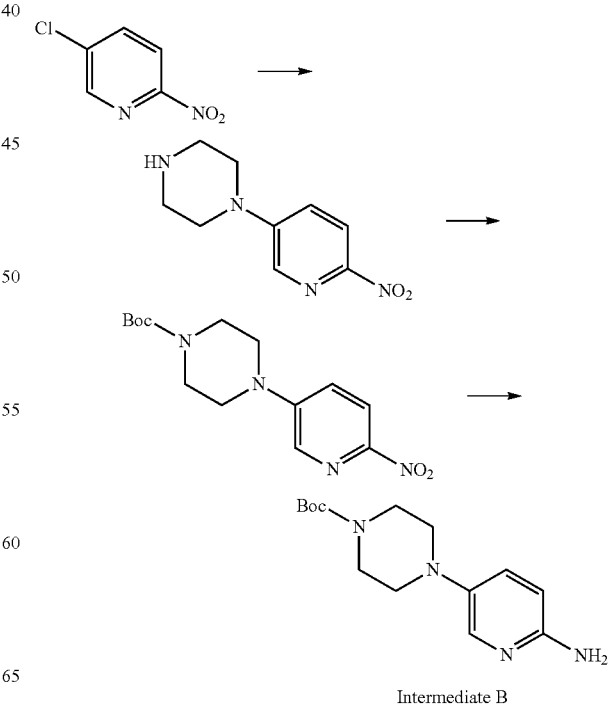

Intermediate B

Synthesis of ribociclib
-continued

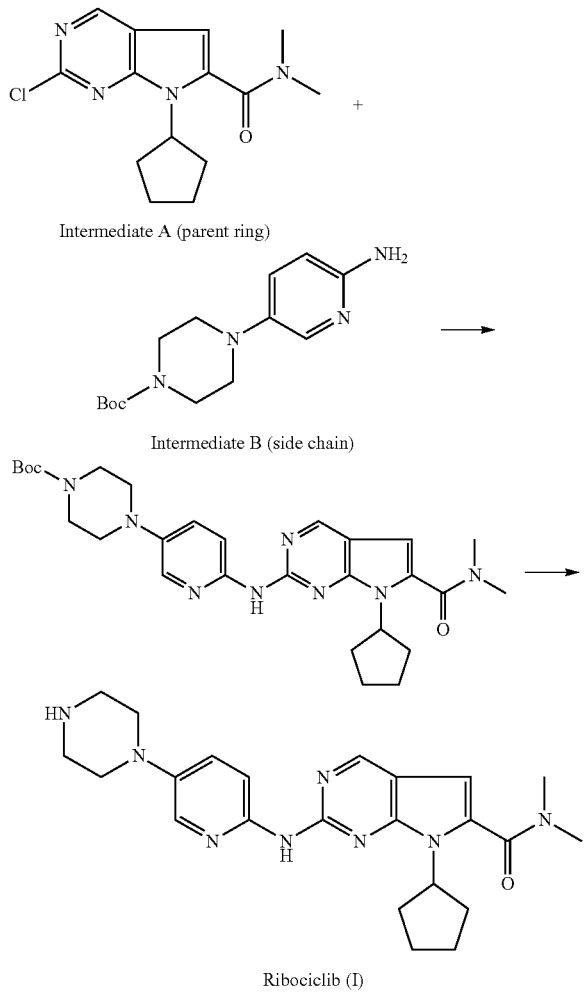

Intermediate A (parent ring)

Intermediate B (side chain)

Ribociclib (I)

By analysis of the above synthetic routes, the intermediate A as a parent ring is prepared in a way that a trihalogenopyrimidine compound and cyclopentylamine are subjected to nucleophilic aromatic substitution reaction, Sonogashira reaction and cyclization reaction under an alkaline condition to obtain a hydroxyl compound of pyrimidine pyrrole, and the compound is then oxidized by manganese dioxide and subjected to a process including amidation reaction and the like in the presence of sodium cyanide to obtain the target intermediate A. Obviously, the preparation process is quite complicated, lots of unconventional reagents require to be used, and particularly, use of a noble metal catalyst and use of the sodium cyanide as a deadly poisonous compound bring great difficulties to industrial production.

For overcoming existing process defects, a preparation technology which is simple in process, economical and environmentally friendly, and high in quality is developed, and particularly, a process technology capable of adapting to industrial production needs to be sought, and is of great realistic significance on improvement of the economic and social benefits of the drug.

SUMMARY OF THE INVENTION

The invention aims to provide a ribociclib preparation method which has the advantages of accessible raw materials, simple process and high economy and environmental friendliness, and is suitable for industrial production.

In order to achieve the above objective, a compound N-cyclopentyl-2-methoxy-5-(N,N-dimethyl-formamido)-3-pyrrylformonitrile as shown in a formula II is prepared at first in the invention,

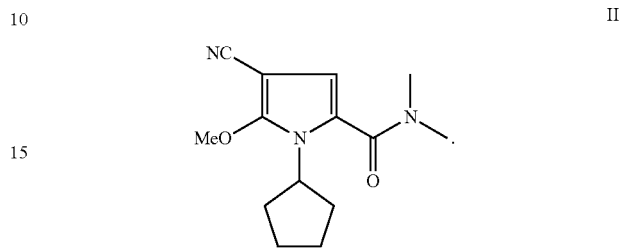

The preparation method of the compound N-cyclopentyl-2-methoxy-5-(N,N-dimethyl-formamido)-3-pyrrylformonitrile comprises the following steps: carrying out halogenating reaction on N,N-dimethyl-2-carbonyl-propanamide (IV) to obtain N,N-dimethyl-1-halo-2-carbonyl-propanamide (V); carrying out substitution reaction on the N,N-dimethyl-1-halo-2-carbonyl-propanamide (V) and malononitrile to generate N,N-dimethyl-1,1-dicyano-3-carbonyl-butyramide (VI); carrying out cyclization reaction on the N,N-dimethyl-1,1-dicyano-3-carbonyl-butyramide (VI) by using methanol as a solvent to obtain 2-methoxy-5-(N,N-dimethyl-formamido)-3-pyrrylformonitrile (VII); and carrying out coupling reaction on the 2-methoxy-5-(N,N-dimethyl-formamido)-3-pyrrylformonitrile (VII) and bromocyclopentane to obtain the N-cyclopentyl-2-methoxy-5-(N,N-dimethyl-formanido)-3-pyrrylformonitrile (II).

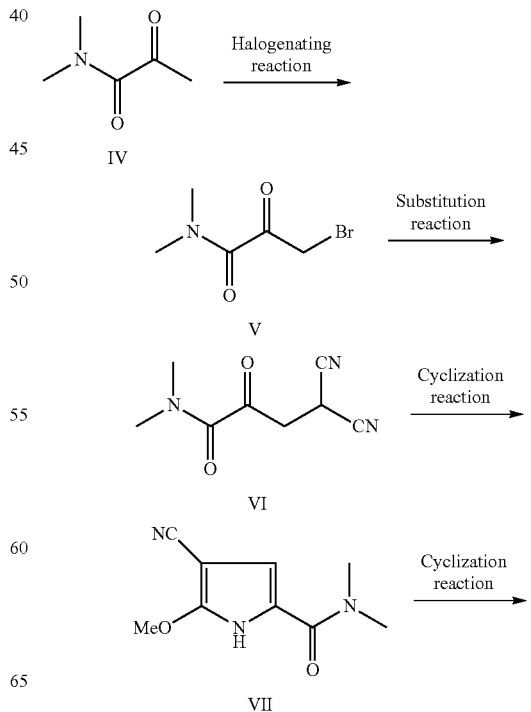

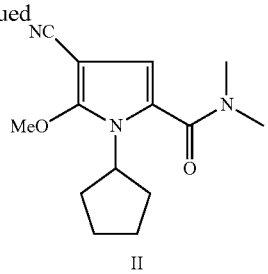

II

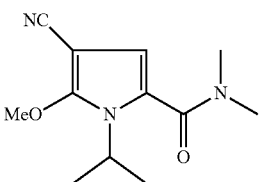

(II)

In addition, the invention further proposes the following subordinate technical solution:

A halogenating agent for the halogenating reaction is fluorine, chlorine, bromine or iodine, and is chlorine or bromine preferably.

An acid-binding agent for the substitution reaction is triethylamine, pyridine, N-methylmorpholine, diisopropyl-ethylamine, 4-dimethylaminopyridine, potassium carbonate, lithium carbonate, potassium tert-butoxide or sodium hydride.

A temperature for the cyclization reaction is −25° C. to 25° C., and is 0-10° C. preferably. A molar ratio of raw materials including the 2-methoxy-5-(N,N-dimethyl-formamido)-3-pyrrylformonitrile (VII) and the bromocyclopentane for the coupling reaction is 1:1.5-2.5, and is 1:2.0 preferably.

An alkali accelerator for the coupling reaction is sodium hydride, potassium hydride, sodium hydroxide, potassium hydroxide, sodium tert-butoxide, potassium tert-butoxide, sodium methylate, sodium ethylate, sodium carbonate, potassium carbonate or cesium carbonate, and is potassium tert-butoxide or cesium carbonate preferably.

A solvent for the coupling reaction is dichloromethane, 1,2-dichloroethane, acetonitrile, methylbenzene, tetrahydrofuran, dimethyl carbonate, dioxane or N,N-dimethylformamide, and is N,N-dimethylformamide preferably.

Meanwhile, the invention further provides a method for preparing ribociclib (I) by using the intermediate N-cyclopentyl-2-methoxy-5-(N,N-dimethyl-formamido)-3-pyrrylformonitrile (II),

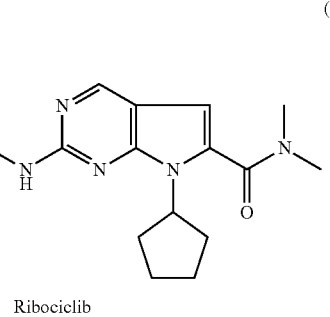

Ribociclib

The preparation steps include: carrying out condensation reaction on the N-cyclopentyl-2-methoxy-5-(N,N-dimethylformamido)-3-pyrrylformonitrile (II) and N-[5-(1-piperazino)-2-piperidyl]guanidine (III) to obtain ribociclib (I).

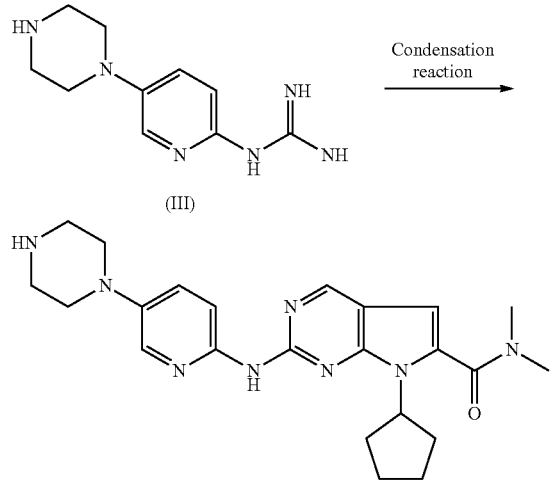

Ribocilib (I)

A molar ratio of raw materials including the N-cyclopentyl-2-methoxy-5-(N,N-dimethyl-formamido)-3-pyrrylformonitrile (II) and the N-[5-(1-piperazino)-2-piperidyl] guanidine (III) for the condensation reaction is 1:1.0-3.0, and is 1:1.5-2.5 preferably.

A temperature of the condensation reaction is 50-150° C., and is 90-130° C. preferably. A solvent for the condensation reaction is dimethylbenzene, dioxane, N,N-dimethylformamide, N,N-dimethylacetamide or dimethylsulfoxide, and is methylbenzene or dimethylbenzene preferably.

Compared with the prior art, the preparation method for ribociclib (I) involved in the invention has the advantages of accessible raw materials, simple process, high economy and environmental friendliness, therefore, industrial production of the crude drug is facilitated, and development of the economic technology is promoted.

DETAILED DESCRIPTION OF THE INVENTION

The technical solution of the invention will be further described in detail in a non-limiting manner with reference to several preferred examples below.

Preparation of raw material N,N-dimethyl-2-carbonyl-propanamide (IV) can refer to preparation of the same compound in the literature Journal of Organic Chemistry, 69(16), 5509-5511; 2004; and preparation of a raw material N-[5-(1-piperazino)-2-piperidyl] guanidine (III) can refer to a preparation method of the same compound of international invention patent WO2006095159 which was named as '(Imidazole-5-yl)-2-anilo-pyrimidines as agents for the inhibition of cell proliferation' and was published on Sep. 14, 2006.

Example 1

N,N-dimethyl-2-carbonyl-propanamide (IV) (5.75 g, 50 mmol), 0.1 g of 98% concentrated sulfuric acid and 30 mL of tetrahydrofuran were added in a drying reaction bottle, and were heated to a temperature of 50-55° C. Bromine (7.9 g, 55 mmol) which was dried by concentrated sulfuric acid in advance was dropwise added during stirring, after dropwise adding of the bromine was finished, stirring reaction was continued for 3-5 hours while the temperature is kept until the color of bromine fades out basically, and then reaction was finished. A solvent was recycled under reduced pressure, residues were recrystallized with ethyl acetate and n-hexane (1:1, V/V), and were dried under vacuum at room temperature to obtain faintly yellow solid N,N-dimethyl-1-halo-2-carbonyl-propanamide (V) 8.3 g, and the yield was 86.0%; and EI-MS m/z: 193[M+H]$^+$.

Example 2

N,N-dimethyl-1-halo-2-carbonyl-propanamide (V) (5.8, 30 mmol), malononitrile (2.2 g, 33 mmol), diethylamine (6.6 g, 90 mmol) and silicon dioxide 15 g were added in a reaction bottle, and were ground and stirred for 30 minutes at room temperature to finish TLC detection reaction. Chloroform 100 mL was added in the reaction bottle, filtering is performed after stirring, a filter cake was washed with chloroform for three times, organic phases were merged, were washed with water and a saturated salt solution successively, were dried with anhydrous sodium sulfate, were concentrated, and were dried under vacuum to obtain off-white solid N,N-dimethyl-1,1-dicyano-3-carbonyl-butyramide (VI) 4.5 g, and the yield was 83.8%; and EI-MS m/z: 180 [M+H]$^+$.

Example 3

N,N-dimethyl-1,1-dicyano-3-carbonyl-butyramide (VI) (3.6 g, 20 mmol) and methanol 50 mL were added in a reaction bottle, were cooled to a temperature of 4-7° C. by ice bath, were slowly fed with hydrogen chloride gas (5.4 g, 0.15 mol) during stirring, were heated to room temperature after being fed with the hydrogen chloride gas, and were continuously subjected to stirring reaction for 24-26 hours to finish TLC detection reaction. Nitrogen was fed to remove excessive hydrogen chloride gas, concentration is performed to obtain viscous fluid, the viscous fluid was recrystallized with methanol and water (1:1) to obtain faintly yellow solid 2-methoxy-5-(N,N-dimethyl-formamido)-3-pyrrylformonitrile (VII) 3.3 g, and the yield was 90.2%; and mass spectrum (EI): EI-MS m/z: 194 [M+H]$^+$.

Example 4

2-methoxy-5-(N,N-dimethyl-formamido)-3-pyrrylformonitrile (VII) (1.9 g, 10 mmol), bromocyclopentane (3.0 g, 20 mmol), cesium carbonate (6.5 g, 20 mmol) and N,N-dimethylformamide 25 mL were added in a reaction bottle, were heated to a temperature of 70-80 step by step, and were subjected to stirring reaction for 26-30 hours to finish TLC detection reaction. Cooling was performed, 50 mL of ethyl acetate and 50 mL of water were added, and a water phase was separated out, and then was extracted twice with ethyl acetate. Organic phases were merged, were washed with water and a saturated salt solution successively, were dried with anhydrous sodium sulfate, and then were concentrated, obtained grease was recrystallized with ethyl acetate and n-hexane (2:1), and was dried under vacuum to obtain off-white solid N-cyclopentyl-2-methoxy-5-(N,N-dimethyl-formamido)-3-pyrrylformonitrile (II) 1.85 g, and the yield was 70.9%; and EI-MS m/z: 262[M+H]$^+$, $^1$H NMR (CDCl$_3$) δ1.70-1.97 (m, 4H), 1.99 (m, 4H), 3.08 (s, 6H), 3.26 (s, 3H), 4.76-4.65 (m, 1H), and 6.54 (s, 1H).

Example 5

In a nitrogen atmosphere, N-cyclopentyl-2-methoxy-5-(N,N-dimethyl-formamido)-3-pyrrylformonitrile (II) (2.6 g, 10 mmol), N-[5-(1-piperazino)-2-piperidyl] guanidine (III) (4.4 g, 20 mmol) and dimethylbenzene 15 mL were added in a reaction bottle, were heated to 120° C., and were subjected to stirring reaction for 20-24 hours to finish TLC detection reaction. A solvent was distilled off under reduced pressure, and was cooled to room temperature, methanol was added, and solid was separated out. The solid was filtered, a filter cake was washed twice with cold methanol, and was dried under vacuum to obtain off-white solid ribociclib (I) 3.05 g, and the yield was 70.3%; and EI-MS m/z: 435 [M+H]$^+$, $^1$H NMR (DMSO-d6) δ1.63 (m, 2H), 1.99 (m, 4H), 2.50 (m, 2H), 3.05 (m, 10H), 3.28 (m, 4H), 4.62 (m, 1H), 6.24 (s, 1H), 7.47 (m, 1H), 8.03 (m, 1H), 8.21 (m, 1H), 8.78 (s, 1H) and 9.42 (s, 1H).

It should be noted that the examples discussed above are merely for describing the technical concept and features of the invention, their objective is that those skilled in the art could understand the content of the invention and implement therefrom, and limitation to the patent scope of the invention cannot be made by these examples. All equivalent changes or modifications according to the spirit of the invention should fall within the extent of protection of the invention.

What is claimed is:

1. A compound N-cyclopentyl-2-methoxy-5-(N,N-dimethyl-formamido)-3-pyrrylformonitrile as shown in a formula II

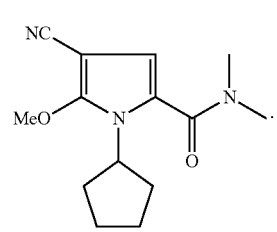

II

2. The compound N-cyclopentyl-2-methoxy-5-(N,N-dimethyl-formamido)-3-pyrrylformonitrile according to claim 1, wherein a preparation method of the compound N-cyclopentyl-2-methoxy-5-(N,N-dimethyl-formamido)-3-pyrrylformonitrile comprises the following steps: carrying out halogenating reaction on N,N-dimethyl-2-carbonyl-propanamide to obtain N,N-dimethyl-1-halo-2-carbonyl-propanamide; carrying out substitution reaction on the N,N-dimethyl-1-halo-2-carbonyl-propanamide and malononitrile under the effect of an acid-binding agent to prepare N,N-dimethyl-1,1-dicyano-3-carbonyl-butyramide; carrying out cyclization reaction on the N,N-dimethyl-1,1-dicyano-3-carbonyl-butyramide by using methanol as a solvent to prepare 2-methoxy-5-(N,N-dimethyl-formamido)-3-pyrrylformonitrile; and carrying out coupling reaction on the 2-methoxy-5-(N,N-dimethyl-formamido)-3-pyrrylformonitrile and bromocyclopentane under the effect of an alkali accelerator to obtain the N-cyclopentyl-2-methoxy-5-(N,N-dimethyl-formanido)-3-pyrrylformonitrile (II).

3. The compound N-cyclopentyl-2-methoxy-5-(N,N-dimethyl-formamido)-3-pyrrylformonitrile according to claim 2, wherein a halogenating agent for the halogenating reaction is fluorine, chlorine, bromine or iodine.

4. The compound N-cyclopentyl-2-methoxy-5-(N,N-dimethyl-formamido)-3-pyrrylformonitrile according to claim 2, wherein the acid-binding agent for the substitution reaction is triethylamine, pyridine, N-methylmorpholine, diisopropylethylamine, 4-dimethylaminopyridine, potassium carbonate, lithium carbonate, potassium tert-butoxide or sodium hydride.

5. The compound N-cyclopentyl-2-methoxy-5-(N,N-dimethyl-formamido)-3-pyrrylformonitrile according to claim 2, wherein a molar ratio of raw materials including the 2-methoxy-5-(N,N-dimethyl-formamido)-3-pyrrylformonitrile and the bromocyclopentane for the coupling reaction is 1:1.5-2.5.

6. The compound N-cyclopentyl-2-methoxy-5-(N,N-dimethyl-formamido)-3-pyrrylformonitrile according to claim 2, wherein a temperature for the coupling reaction is −25 to 25° C.

7. The compound N-cyclopentyl-2-methoxy-5-(N,N-dimethyl-formamido)-3-pyrrylformonitrile according to claim 2, wherein the alkali accelerator for the coupling reaction is sodium hydride, potassium hydride, sodium hydroxide, potassium hydroxide, sodium tert-butoxide, potassium tert-butoxide, sodium methylate, sodium ethylate, sodium carbonate, potassium carbonate or cesium carbonate.

8. The compound N-cyclopentyl-2-methoxy-5-(N,N-dimethyl-formamido)-3-pyrrylformonitrile according to claim 2, wherein the solvent for the coupling reaction is dichloromethane, 1,2-dichloroethane, acetonitrile, methylbenzene, tetrahydrofuran, dimethyl carbonate, dioxane or N,N-dimethylformamide.

9. The compound N-cyclopentyl-2-methoxy-5-(N,N-dimethyl-formamido)-3-pyrrylformonitrile according to claim 1, wherein the compound N-cyclopentyl-2-methoxy-5-(N,N-dimethyl-formamido)-3-pyrrylformonitrile of the formula II and N-[5-(1-piperazino)-2-piperidyl]guanidine are subjected to condensation reaction to prepare ribociclib

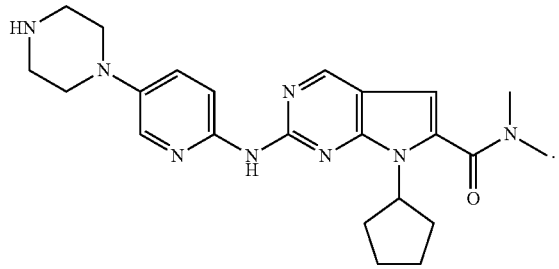

Ribociclib

10. The compound N-cyclopentyl-2-methoxy-5-(N,N-dimethyl-formamido)-3-pyrrylformonitrile according to claim 9, wherein a molar ratio of raw materials including the N-cyclopentyl-2-methoxy-5-(N,N-dimethyl-formamido)-3-pyrrylformonitrile and the N-[5-(1-piperazino)-2-piperidyl]guanidine for the condensation reaction is 1:1.0-3.0.

11. The compound N-cyclopentyl-2-methoxy-5-(N,N-dimethyl-formamido)-3-pyrrylformonitrile according to claim 9, wherein a temperature for the condensation reaction is 50-150° C.; and a solvent for the condensation reaction is dimethylbenzene, dioxane, N,N-dimethylformamide, N,N-dimethylacetamide or dimethylsulfoxide.

* * * * *